United States Patent [19]

Lai

[11] 4,310,429
[45] Jan. 12, 1982

[54] STABILIZED POLYMERS, NOVEL STABILIZERS, AND SYNTHESIS THEREOF

[75] Inventor: John T. Lai, Broadview Heights, Ohio

[73] Assignee: The B. F. Goodrich Company, Akron, Ohio

[21] Appl. No.: 916,639

[22] Filed: Jun. 19, 1978

[51] Int. Cl.³ .......................... C10M 1/32; C10M 1/24
[52] U.S. Cl. ............................... 252/51.5 A; 564/164; 564/193; 564/197; 564/201; 260/326.2; 260/326.4; 260/326.8; 546/184; 546/192; 548/255; 548/362; 544/358; 544/359; 544/106; 252/56 S; 564/163; 564/165; 564/194; 564/195
[58] Field of Search ............ 260/561 A, 558 A, 326.4, 260/326.2, 326.8; 252/51.5 A; 564/164, 193, 197; 546/184, 192; 548/255, 262; 544/358, 359, 106

[56] References Cited

U.S. PATENT DOCUMENTS

| | | | |
|---|---|---|---|
| 2,139,190 | 12/1938 | Iselin et al. | 260/561 A |
| 2,153,707 | 4/1939 | Becherer et al. | 260/561 A X |
| 2,499,352 | 3/1950 | Bruce et al. | 260/558 A |
| 2,548,863 | 4/1951 | Bruce et al. | 564/197 |
| 3,247,200 | 4/1966 | Ugi et al. | 260/558 A X |
| 3,361,812 | 1/1968 | Hofer et al. | 564/193 X |
| 3,428,646 | 2/1969 | Hellerbach | 260/558 A X |
| 3,446,806 | 5/1969 | Archer et al. | 564/164 X |
| 3,625,972 | 12/1971 | Schulenberg | 260/558 A X |
| 3,674,787 | 7/1972 | Frey et al. | 260/568 A X |
| 3,676,492 | 7/1972 | Biel et al. | 564/164 X |
| 3,919,313 | 11/1975 | Villani | 564/193 X |
| 3,944,607 | 3/1976 | Chan | 260/558 A |
| 4,064,270 | 12/1977 | Wollweber et al. | 260/558 A X |
| 4,072,698 | 2/1978 | Hylton et al. | 564/164 X |
| 4,205,168 | 5/1980 | Chan | 260/558 A X |

*Primary Examiner*—Paul F. Shaver
*Attorney, Agent, or Firm*—Alfred D. Lobo; J. Hughes Powell, Jr.

[57] ABSTRACT

Novel α-aminoacetamides are powerful stabilizers for organic materials subject to oxygen and heat degradation, and particularly for synthetic natural rubber and synthetic ester lubricants. A wide range of substituents on the amine and amide N atoms, and also on the saturated carbon atom, yields an array of stabilizers having a wide range of compatibility in compositions comprising various synthetic resinous compounds to be stabilized.

Novel syntheses are provided utilizing at least one amine nucleophilic agent, a dichlorocarbene ion generating agent, and an alkoxide ion generating agent, which together in the presence of aqueous alkali and an onium salt, yield novel α-aminoacetamides in which a wide choice of substituents may be introduced. The nucleophilic agent may be a primary or secondary amine, or one of each. The dichlorocarbene ion generating agent is a haloform. The alkoxide ion generating agent may be a ketone, an aldehyde, or a cyanohydrin which reacts with the haloform. An α-trihalomethyl alcohol also reacts with the amine nucleophilic agent, without the benefit of a dichlorocarbene ion generating agent. When the alkoxide ion generating agent is an α-trihalomethyl alcohol, an α-hydrogen may optionally be substituted.

35 Claims, No Drawings

STABILIZED POLYMERS, NOVEL STABILIZERS, AND SYNTHESIS THEREOF

BACKGROUND OF THE INVENTION

Any material, whether natural or synthetic must exhibit satisfactory resistance to degradation under conditions of use, if products made from the materials are to find a lasting market. A lack of satisfactory resistance to degradation usually manifests itself as a partial or total loss of structure integrity, a darkening or discoloration of the product, a loss of flexibility or resilience, or a combination of the above phenomena. These phenomena are promoted or catalyzed by air (oxygen), heat and light, and are particularly susceptible to autooxidation at elevated temperatures in the presence of oxygen.

To protect organic materials, ingredients which can be collectively called stabilizers are admixed with the materials to prevent or inhibit degradation. These stabilizers work in diverse and complex ways, such that a compound which stabilizes against oxygen degradation in one type of material may be relatively inactive in another type of material. Thus compounds which are stabilizers are further classed as anti-oxidants, antiozonants, heat stabilizers and ultraviolet (UV) light stabilizers, depending upon what type of activity and stabilization they best demonstrate. In many cases, to obtain optimum protection, a mixture of compounds, each specifically selected to afford maximum protection against a certain type of degradation, is often used. In some instances stabilizers are deliberately chosen to counter the adverse effects of a plasticizer which, though highly effective as a plasticizer, tends to accelerate oxygen and heat degradation. In other words, the plasticized material is more susceptible to degradation than if no plasticizer was added. As a general empirical rule, it is found that plasticizers are marginally effective as stabilizers, and stabilizers are marginally effective as plasticizers, it being more likely that a compound with desirable stabilizer properties has undesirable plasticizer properties, and vice versa.

The stabilization of rubber, and particularly synthetic "natural rubber", is essential for its proper functioning and long life. To protect rubber against deterioration, many new compounds have been synthesized and tested. Although most anti-oxidants give good protection as stabilizers, not all stabilizers give satisfactory anti-oxidant activity (Encyclopedia of Polymer Science and Technology, Vol. 12, btm p 267, Interscience Publishers, New York, 1970). The compounds of this invention are primarily antioxidants though they exhibit other desirable stabilizing properties, and are particularly for use in synthetic ester lubricants, generally known as "functional fluids", and in synthetic diene rubbers, as a primary antioxidant, i.e. as the sole antioxidant, or if desired, may be combined with a secondary antioxidant which serves to enhance the stabilizing performance of the primary antioxidant. When used with a secondary antioxidant, the stabilizing effect achieved is synergistic and the performance substantially exceeds the sum total of the performances exhibited by the individual antioxidant components.

The time-tested rubber antioxidants chemically classed as amines and phenols and their respective derivatives are still being used, but newer antioxidants combine a hindered phenol group with another group containing sulfides, triazine, phosphates, phosphites, etc. with the hope that the active materials will combine the advantages of two or more stabilizing moieties.

The compounds of this invention do not belong to any well-recognized chemical class of antioxidants. They are substituted acetamides, and more particularly substituted α-aminoacetamides. It is worth noting that known antioxidants formed by reactions of aldehyde-amines have only fair oxygen aging, and reaction products of ketone-amines generally have only good oxygen aging (Kirk & Othmer, Encyclopedia of Chemical Technology, 2d Edition, Vol 17, p 526, Interscience Publishers, New York, 1968).

As is well-known to those skilled in the art, the effectiveness of an antioxidant organic is predicated upon the oxidizable material in which the antioxidant is used. Thus, though antioxidants are used in plastics, elastomers, petroleum products, synthetic lubricants, food products, paints, soaps and cosmetics, it is seldom that the same type of antioxidant will be useful in a plastic or elastomer, and a petroleum or synthetic lubricant. Yet the compounds of this invention provide just such a multifunctional purpose, being useful in several synthetic resinous materials including plastics, elastomers and particularly conjugated diene polymers and synthetic functional fluids of the type generally classed as di- and polycarboxylate type ester lubricants.

Various amides have been found useful as antioxidants. For example, water-soluble antioxidants such as amides of phenol substituted acids have been produced by reaction of reactive derivatives of corresponding acids with corresponding amino compounds to form acid amides, as disclosed in U.S. Pat. No. 3,665,031. Conventional methods of amide preparation also yield alkylhydroxybenzylamides as taught in U.S. Pat. No. 3,780,103. A reaction between selected alkylaminophenols and thiodialkanoyl acid chlorides yields thiodialkanoamidophenol compounds; related compounds are disclosed in U.S. Pat. Nos. 3,676,494; 3,679,744 and 3,694,375. None of the foregoing conventional methods of amide preparation yields the compounds of this invention.

It was known a long time ago, that the reaction of chloretone (1,1,1-trichloro-2-methyl-2-propanol) with aniline and KOH in ethanol, yields α-phenylaminoisobutyric acid anilide, also referred to as α-dimethyl,α-analino,analinoacetamide (see Example 8B herein), though in poor yields. See G. Banti, Gazz. Chim. Ital. 59, 819–24 (1929). Furthermore, this reaction is applicable only to aniline and substituted anilines, and even so, compounds higher in molecular weight than chloretone and aniline, give progressively poorer yields.

The present invention is particularly directed to (a) novel antioxidants and heat stabilizers classed as hindered acetamides, more specifically classed as hindered alpha-aminoacetamides, (b) novel compositions in which the α-aminoacetamides are incorporated, and (c) novel syntheses for the α-aminoacetamides. The basic structure of these novel compounds is an α-aminoacetamide which is preferably polysubstituted. Though these novel compounds are acyclic, they may have cyclizable substituents, and may form dimers and bis-compounds. The novel compounds of this invention are unrelated to amino acids and are not derived from them.

The synthesis of the novel stabilizers of this invention is made possible by the peculiar action of certain onium salts in an aqueous alkaline medium, which action facilitates the interaction of an amine nucleophilic agent such as a primary or secondary amine, with chloroform or other dichlorocarbene generating agent, and a ketone, aldehyde, cyanohydrin or other alkoxide ion generating agent. The organic onium salts of nitrogen, phosphorus and sulfur are well known. They are ionized in aqueous solutions to form stable cations. Certain onium salts have provided the basis for phase transfer catalysis in a wide variety of reactions, a recent and comprehensive review of which is contained in Angewandte Chemie, International Edition in English, 16 493–558 (August 1977). Discussed therein are various anion transfer reactions where the onium salt exchanges its original anion for other anions in the aqueous phase. These ion pairs can then enter a water immiscible, organic liquid phase, making it possible to carry out chemistry there with the transported anion, including OH$^-$ ions. Many reactions involving water immiscible solutions of various simple organic molecules have been described. However, there is nothing to suggest the phase transfer catalysis of the reactants described in my invention.

SUMMARY OF THE INVENTION

Substituted α-aminoacetamides have been discovered which are excellent stabilizers for organic materials, and especially for conjugated diene polymers and lubricants known as "functional fluids" of the synthetic polycarboxylate type. Specific conjugated diene polymers are natural and synthetic rubbers such as are used in the manufacture of vehicle tires, belting, rubber hose and the like. Specific functional fluids of the polycarboxylate type are those having from 2 to about 8 carboxylate groups per molecule.

Novel compositions have been discovered comprising an organic material subject to the deleterious effects of oxygen heat and light, and from about 0.001 percent to about 10 percent by weight of substituted α-aminoacetamides dispersed therein.

It has also been discovered that polysubstituted α-aminoacetamides, may be directly synthesized, catalytically, in the presence of onium salts using readily available starting materials, in conventional apparatus, under ambient temperature and pressure conditions. In these syntheses, an alkoxide ion generating agent selected from the group consisting of a ketone, an aldehyde and a cyanohydrin is reacted with a dichlorocarbene generating agent, e.g. a haloform, under alkaline conditions with an amine nucleophilic agent such as a primary and/or secondary amine in the presence of an onium salt to yield an α-aminoacetamide. As an alternative, an α-trihalomethylhydroxyalcohol, for example trichloromethyl alcohol, optionally suitably substituted, may be used instead of the ketone, aldehyde, or cyanohydrin and the haloform. Substituents on the α-aminoacetamide may be introduced by an appropriate choice of substituents on the alkoxide ion generating agent, and, substituents on the amine nucleophilic agent.

DETAILED DESCRIPTION OF PREFERRED EMBODIMENTS

The substituted acetamides of this invention used to stabilize organic materials are primarily anti-oxidant stabilizers (referred to as 'antioxidants'), and heat stabilizers, which exhibit excellent performance when dispersed in organic materials subject to oxidative, thermal and photochemical degradation. Most particularly these stabilizers are antioxidants for synthetic natural rubber and synthetic ester lubricants, and have a balance of properties which permits the stabilizers to be used primarily as antioxidants and heat stablizers with complementary light-stabilization effects without significant loss of flexibility or abrasion of the stabilized material.

It is especially significant that these relatively low molecular weight compounds contain a substituted amino group attached to an acetamide group, each of which groups may be independently substituted with moieties having not only desirable antioxidant properties, but also heat stablizing properties complemented with suitable solubility and dispersability.

The substituted acetamides are generally oils or high melting crystalline solids soluble in acetone, diethyl ether, dioxane, tetrahydrofuran, carbon tetrachloride, chloroform, aromatic hydrocarbons such as benzene and toluene, but much less soluble in aliphatic hydrocarbons and lower alcohols such as methanol and ethanol. Substituted acetamides are generally insoluble in water; they range in color from white to dark brown when pure.

Certain substituted acetamides are more useful for particular applications than others, due to the compatibility of the acetamides with the organic material to be stabilized. This is the result of a variety of factors such as the type of substituents on the alpha C atom, the particular substituents on the amine N atom, and amide N atom, and the physical properties of the acetamide. The amount of antioxidant employed will vary with the particular material to be stabilized and also the substituted acetamide employed. Generally however, for effective stabilization of organic materials, an amount of the antioxidant used is in the range from about 0.001 percent to about 10 percent by weight (% by weight) based on the weight of organic material. In typical stabilized compositions the amount of substituted acetamide used is in the range from about 0.01 to about 5% by weight.

Compositions of this invention are organic materials which have been stabilized to combat the deleterious effects of thermal or oxidative degradation such as are usually evidenced by discoloration and/or embrittlement. These compositions generally benefit from the inclusion of additional, secondary UV stabilizers to achieve even greater stability against a combination of actinic light, heat and oxygen. Therefore, in conjunction with the stabilizers of this invention, compositions may include UV light stabilizers in the range from about 0.1 part to about 10 parts by weight, and preferably from about 0.2 part to about 5 parts by weight per 100 parts by weight of the organic material. Several types of known UV stabilizers may be used, such as those disclosed in U.S. Pat. Nos. 3,325,448; 3,769,259; 3,920,659; 3,962,255; 3,966,711; 3,971,757; inter alia.

The organic materials to be stabilized may be low or high molecular weight materials, and particularly include homopolymers, copolymers and mixtures thereof. Most preferred examples of organic materials present as the continuous phase, which can be stabilized against thermal and oxidative degradation by substituted acetamides are natural rubber; synthetic rubbers formed from conjugated dienes such as cis-polyisoprene, polybutadiene, styrene-butadiene rubber, dienenitrile rubbers, polyepihalohydrin polymers, and the like; and, functional fluids of the polycarboxylate type formed by reacting a polycarboxylic acid with a monohydric alcohol, or alternatively, by reacting a monocarboxylic acid with a polyhydric alcohol.

Illustrative of the functional fluids which can be employed in the present invention are the following dicarboxylates such as oxalates, malonates, succinates, glutarates, adipates, pimelates, suberates, azelates, sebacates and the like; tricarb-oxylates such as the triesters of trimethylolpropane and tricarboxypentane, tetra-carboxylates such as the tetraesters of pentaerythritol, and the higher polycarb-oxylates such as the esters of di- and tripentaerythritol. Mixtures of these esters can also be employed. When a polycarboxylic acid is used to make the polycarboxylate, the alcohol moiety of these esters normally has between 4 and 18 carbon atoms and preferably from 6 to 12 carbon atoms. Likewise, when a polyhydric alcohol is used to make the polycarboxylate, the carboxylic moiety normally has from 4 to 18 carbon atoms and preferably from 4 to 12 carbon atoms. Mixtures of the above described esters can also be used. The preferred base stocks are of the trimethylolpropane and pentaerythritol ester type. Particularly preferred is a mixture of trimethylopropane triheptanoate and pentaerythritol monobutyrate triheptanoate. These esters can also be cross-linked by employing a cross-linking agent such as azelaic acid when synthesizing them as is well known in the art.

The base stocks into which the present antioxidants are incorporated can also contain minor amounts by weight of hydrocarbon lubricants and other well known functional fluid additives. Typical of these latter additives are the following, with the normal ranges in weight percent of the entire fluid being given in the parenthesis:

(a) Viscosity index improvers such as the polymers of acrylic and metha-crylic acid esters which are normally incorporated in a suitable carrier (0.5–5%);

(b) Lubricity and extreme pressure additives of the organo phosphorus type, particularly the organic phosphite, phosphonates, phosphates and amine salts thereof, as exemplified by the hydrogen phosphonates, triaryl phosphates and the amine salts of dialkyl phosphorus acid esters (0.1–5%);

(c) Metal deactivators such as benzotriazoles and the N,N'-disalicylidene-dialkyl diamines (0.001–1%); and (d) Antifoaming agents of the silicone variety, particularly the methyl silicones and siloxanes (0.0001 to 0.002%).

Other organic materials which may be stabilized against thermal and oxidative degradation include other copolymers of butadiene with acrylic acid, alkyl acrylates or methacrylates, polyisoprene, polychloroprene, and the like; polyurethanes; vinyl polymers known as PVC resins such as polyvinyl chloride, copolymers of vinyl chloride with vinylidene chloride, copolymers of vinyl halide with butadiene, styrene, vinyl esters, and the like; polyamides such as those derived from the reaction of hexamethylene diamine with adipic or sebacic acid; epoxy resins such as those obtained from the condensation of epichlorohydrin with bisphenols, and the like; ABS resins, polystyrene, polyacrylonitrile, polymethacrylates, poly-carbonates, varnish, phenol-formaldehyde resins, polyepoxides, polyesters, and polyolefin homo-and copolymers such as polyethylene, polypropylene, ethylene-propylene polymers, ethylene-propylenediene polymers, ethylene-vinyl acetate polymers, and the like. The substituted amino amides can also be used to stabilize mixtures and blends of polymeric materials such as ABS resin blends, PVC and polymethacrylate blends, and blends of polyolefin homopolymers and copolymers such as blends of polypropylene in epdm polymers. Most particularly substituted acetamides of this invention are especially useful as antioxidants for synthetic natural rubber and synthetic ester high temperature lubricants.

Many known compounding ingredients may be used along with the substituted acetamide stabilizers in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin, and the like.

The substituted acetamide stabilizers, and the other compounding ingredients if used, can be admixed with organic materials using known mixing techniques and equipment such as internal mixing kettles, a Banbury mixer, a Henschel mixer, a two-roll mill, an extruder mixer, or other standard equipment, to yield a composition which may be extruded, pressed, blowmolded or the like into film, fiber or shaped articles. Standard mixing times and temperatures can be employed. The objective is to obtain intimate and uniform mixing of the components. A favorable mixing procedure to use when adding a substituted acetamide to an organic material is either to dissolve or suspend the compound in a liquid such as hexane or benzene, add it to the organic material in the form of a powder to the solution or suspension, and extruder-mix the stabilized organic material prior to forming the product.

Samples of the compositions can be checked for oxidative and thermal stability by measuring the time to discoloration and/or embrittlement of the sample after aging in an air circlating oven at 140° C., and other standard ASTM tests.

The novel substituted acetamides of this invention may be represented by the general structural formula:

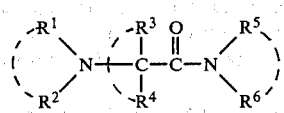

wherein $R^1$, $R^2$, $R^3$, $R^4$, $R^5$ and $R^6$ independently represent the following substituents: hydrogen; aryl, alkyl having from 1 to about 24 carbon atoms wherein functional groups may be substituted with alkyl groups; hydroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; hydroxyalkyl ether or cyanoalkyl ether groups having from 4 to about 18 carbon atoms; alkenyl and aralkyl having from 7 to about 14 carbon atoms; alkylene having from 1 to about 7 carbon atoms; alkenylene having from 2 to about 10 carbon atoms; each substituent optionally containing a phosphite, ester or hindered phenol group, except that each amine and amide N atom has at least one substituent, and said each substituent in combination, $R^1$ with $R^2$, $R^3$ with $R^4$, and $R^5$ with $R^6$, may form a ring containing from about 5 to about 9 ring atoms, which ring may also contain hetero atoms such as N, S or O, and optionally contain a keto, ester, amide, ether or thio group.

By "alkylene" is meant a bivalent group derived by the removal of one H atom from two different carbon atoms of an alkane, but also includes methylene which, as an exception, is obtained by the removal of two H atoms from the same carbon atom. Examples of short chained alkylene substituents are methylene (—$CH_2$—), ethylene (—$CH_2$—$CH_2$—), 1,2-propylene (—$CH_3$—CH—$CH_2$—), 1,3-propylene (—$CH_2$—$CH_2$—$CH_2$—), butylenes and the like. The term "alkenylene" is defined in an analogous manner as "alkylene", except that the H atoms are removed from an alkene. Examples of alkenylene substituents are vinylene (—CH=CH—), propenylene (—$CH_2$—CH=CH—), butenylene, pentenylene, hexenylene, and the like.

Preferred stabilizers are those in which $R^1$ and $R^2$ form a ring, and $R^5$ and $R^6$ form a ring, and each ring comprises only carbon atoms, except for (a) the amine N atom when $R^1$, $R^2$ are cyclized, and (b) the amide N atom when $R^5$, $R^6$ are cyclized. Preferred rings contain 5 or 6 ring atoms, and may be substituted, hence are referred to as optionally substituted rings. Examples of such optionally substituted rings having only one heteroatom, that is N, are those which are derived from pyrrole, pyrrolidone and piperidine. Examples of optionally substituted rings containing more than one heteroatom are those derived from triazole, oxazolidine, piperazine, morpholine and diazepine.

The substituted acetamides of this invention may be grouped as those having:

(A) only one substituent on the alpha C atom;
(B) two substituents on the alpha C atom, each of which may be acyclic;
(C) two substituents on the alpha C atom, one of which is cyclic and the other acyclic; and,
(D) cyclized substituents on the alpha C atom.

The substituted acetamides of this invention may be further grouped as those containing one or more of the following:

(E) two acyclic substituents on the amine N atom;
(F) one cyclic substituent on the amine N atom;
(G) one acyclic substituent on the amine N atom;
(H) two cyclic substituents on the amine N atom;
(I) one cyclic and one acyclic substituent on the amine N atom;
(J) cyclized substituents on the amine N atom;
(K) two acyclic substituents on the amide N atom;
(L) one cyclic substituent on the amide N atom;
(M) one acyclic substituent on the amide N atom;
(N) two cyclic susbstituents on the amide N atom;
(O) one cyclic and one acylic substituent on the amide N atom; and,
(P) cyclized substituents on the amide N atom.

Specific illustrative examples of compounds grouped in the three groups A, E and K are:
α-phenyl,α-diethylaminodiethylacetamide; and,
α-cyclohexyl,α-diethylaminodiethylacetamide.

A specific illustrative example of a compound grouped in the three groups A, G and M is:
α-tolyl-α-propylamino-propylacetamide A specific illustrative example of a compound grouped in the three groups A, I and O is:
α-phenyl-N-methylanilino-N-methylacetanilide.

Specific illustrative examples of compounds grouped in the three groups B, F and K are:
α-dimethyl,α-o-toluidinio-diethylacetamide;
α-dimethyl,α-p-toluidinio-diethylacetamide;
α-dimethyl,α-p-phenetidino-diethylacetamide;
α-dimethyl,α-anilino-diethylacetamide.

A specific illustrative example of a compound grouped in the three groups B, F and L is:
α-dimethyl,α-p-toluidino-acetanilide;
α-dimethyl,α-p-chloroanilino-p-chloroacetanilide;
α-dimethyl,α-anilino-acetanilide;
α-dimethyl,α-toluidino-o-methylacetanilide;
α-dimethyl,α-p-toluidino-p-methylacetanilide; and,
α-dimethyl,α-p-phenetidino-p-ethoxyacetanilide.

A specific illustrative example of a compound grouped in the three groups B, F and M is:
α-dimethyl,α-anilino-propylacetamide.

A specific illustrative example of a compound grouped in the three groups B, F and O is:
α-dimethyl,α-anilino-N-methylacetanilide.

A specific illustrative example of a compound grouped in the three groups B, F and N is:
α-dimethyl-α-anilino-dicyclohexylacetamide.

A specific illustrative example of a compound grouped in the three groups B, J and P is:
α-dimethyl-α-morpholino-acetamorpholinide.

A specific illustrative example of a compound grouped in the three groups C, F and L is:
α-methyl-α-phenyl-α-anilino-acetanilide.

Specific illustrative examples of compounds grouped in the three groups D, F and L are:
α-pentamethylene,α-anilino-acetanilide; and,
α-pentamethylene,α-toluidino-tolylacetamide.

From the foregoing illustrative examples it will now be evident that various combinations of the above identified groups may be produced in a wide range of compounds. Those skilled in the art will appreciate that some compounds are more easily prepared than others, being affected by such considerations as steric hindrance, basicity of reactants, formation of byproducts, and the like. Of essential significance is the fact that, with a little routine trial and error, a substituent deemed likely to have a beneficial effect in a particular substituted acetamide to be used in a particular organic material, may be introduced directly due to the catalytic action of an onium salt in an alkaline aqueous medium. In particular, dimers and bis compounds of the substituted acetamides may also be prepared by known methods once the desired acetamide is obtained by a chosen onium salt catalyzed synthesis. A dimer may be linked through any of the substituents $R^1$–$R^6$. The compounds of this invention may be further modified with additional steps well known to those skilled in the art.

In each preferred embodiment, the substituted acetamides are conveniently prepared from an amine nucleophilic agent and an alkoxide ion generating agent at ambient conditions only in the critical presence of an onium salt under aqueous alkaline conditions. By aqueous alkaline conditions I refer to an aqueous solution of an alkali metal hydroxide containing from about 5% to about 75% by wt, and preferably from about 30% to about 50% by wt of alkali metal hydroxide. Preferred alkali metal hydroxides are those of sodium and potassium. By an amine nucleophilic agent I refer to an amine which is capable of attacking the epoxide ring, which it is hypothesized is formed as an intermediate under the alkaline conditions of this reaction. Primary and secondary amines are such agents.

It is critical for the overall reaction to occur, that an onium salt be present in an aqueous alkaline medium. Onium salts of sulfur, or of any element of Group VA of the Periodic Table, having certain structural limitations, may be used in which a preferred salt has the formula $R_nY^+X^-$, where Y is chosen from N P and S; R represents either different or identical monovalent organic radicals bonded to Y by covalent linkages; $X^-$ is a counterion; and n is an integer which may be 3 or 4. When Y is pentavalent, for example P or N, then $n=4$, and when Y is tetravalent, for example S, then $n=3$. In an analogous manner, onium salts having certain multivalent organic substituents may be useful in this invention. Examples include multivalent organic radicals that include Y in a ring, and those that are bonded to more than one Y.

More preferred onium salts for use in this invention have the formula $(R_aR_bR_cR_dY^+) X^-$ wherein Y is N or P, and $R_a$–$R_d$ are monovalent hydrocarbon radicals preferably selected from the group consisting of alkyl, alkenyl, aryl, alkaryl, aralkyl, and cycloalkyl moieties or radicals, optionally substituted with suitable heteroatom-containing functional groups. The total number of carbon atoms in $R_a$, $R_b$, $R_c$, and $R_d$ if the salt is quaternary, should be at least 10 and is preferably in the range from about 15 to 40. No theoretical maximum number of carbon atoms or inclusion in the onium salts exists, although in general, about 70 carbon atoms represents the upper limit imposed by practical limitations. Since the liquid phases involved are aqueous and organic, the number of the carbon atoms and structure of the onium salts are usually selected to impart to the salt a marked solubility in the organic phase. The onium salt itself is nonreactive with respect to all materials in the reaction mixture except the reactants themselves.

Most preferred onium salts have $Y=N$, and hydrocarbon radicals where $R_a$ is $C_2H_5$, and $R_b$, $R_c$, and $R_d$ are each selected from the group consisting of n-$C_4H_5$; n-$C_5H_{11}$; mixed $C_5H_{11}$; n-$C_6H_{13}$; mixed $C_6H_{13}$; $C_6H_5$; $C_6H_5CH_2$; n-$C_8H_{17}$; n-$C_{12}H_{25}$; n-$C_{18}H_{37}$; mixed $C_8$-$C_{10}$ alkyl; and the like. However, $R^1$ may also be selected from $C_2H_5$, n-$C_3H_7$ and n-$C_4H_9$.

Various counterions may be used, including $Cl^-$, $Br^-$, $I^-$, $F^-$, $SO_4^=$, $HSO_4^-$ and the like. Most preferred is $Cl^-$.

In addition to the above-described specific structure of the onium salt, the amount of the salt used in the range from about 0.01 mol to about 10 mols, and more preferably, for the usual practice of this invention, from about 1 to about 3 mpha (mols per 100 mols of amine nucleophilic agent) used. The amount of salt used is not critical, the optimum amount in each case being easily determined by simple trial and error. An amount greater than about 10 mpha is uneconomical and serves no useful purpose.

In one preferred embodiment, an amine nucleophilic agent, whether a primary or a secondary amine, or one of each, is reacted with a ketone or aldehyde, and a haloform to yield a substituted acetamide. The precise mechanism of the reaction is not fully understood, but a mechanism is hypothesized.

The overall reaction which occurs with different secondary amines, a ketone and chloroform requires equimolar amounts of chloroform and amine nucleophilic agent, and may be represented as follows:

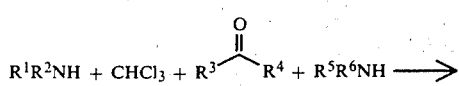

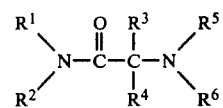

where the reaction occurs in an aqueous alkaline solution of an onium salt present in an amount in the range from about 0.01 to about 10 mole percent based on 100 moles of nucleophilic agent.

The foregoing reaction may be represented as occurring in a series of steps which may be set forth as follows: Amine I attaches to dichlorocarbene generated from chloroform, in the aqueous alkaline medium, to form ion II, thus:

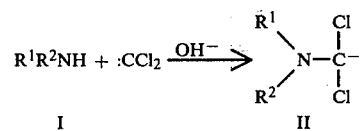

Ion II attacks the ketone to generate the alkoxide ion II, thus:

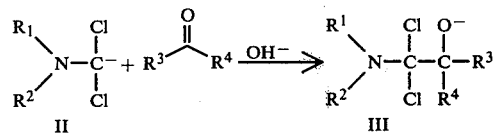

The ion III loses a chlorine to form an epoxide IV which is opened by attack of the amine V to obtain the product, thus:

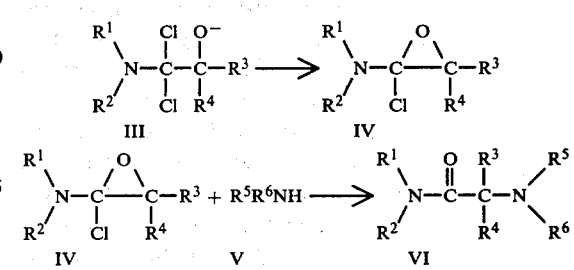

Thus, it will now be evident that a wide variety of substituents may be introduced into VI by choice of appropriate nucleophilic agents I and V, and a ketone which permits the foregoing sequence of reactions. In an analogous manner, an aldehyde which is desirably substituted, may be used in place of the ketone with similar results.

In another preferred embodiment, an amine nucleophilic agent, whether a prior or secondary amine, or one of each, is reacted with a cyanohydrin and a haloform to yield a substituted acetamide. A preferred haloform is selected from the group consisting of chloroform and bromoform, with chloroform being most preferred.

The overall reaction which occurs with different secondary amines, a cyanohydrin and chloroform, requires two mols of $CHCl_3$ per mol of nucleophilic agent, and may be represented as follows:

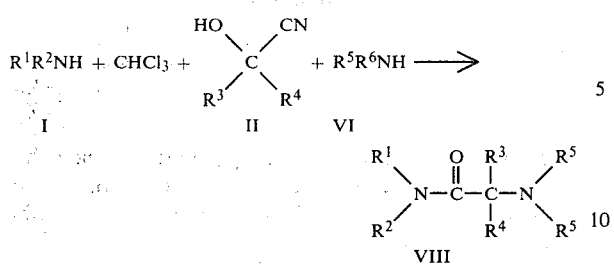

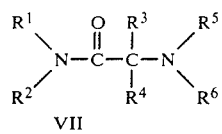

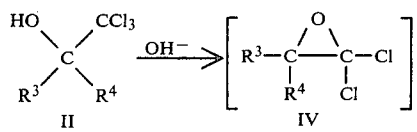

The foregoing reaction may be hypothesized to occur in a series of steps which may be set forth as follows:

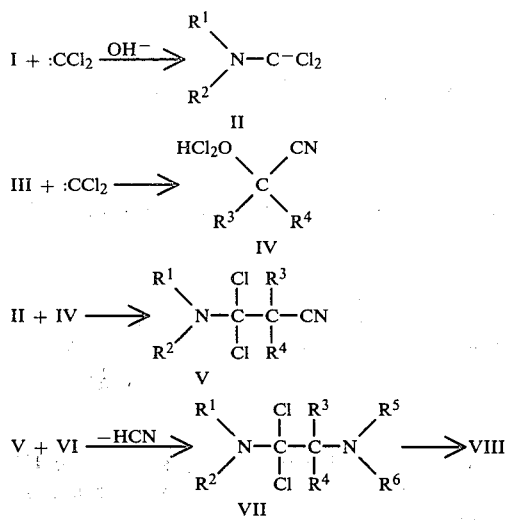

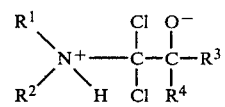

The amine I attacks the epoxide ring in IV giving

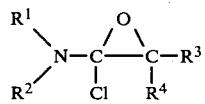

Ion V loses a chlorine forming an epoxide

In still another preferred embodiment, an amine nucleophilic agent, whether a primary or secondary amine, or one of each, is reacted only with an α-trihalomethyl alcohol R³R⁴C(OH)CQ₃, where Q represents halogen. Substituents R³ and R⁴ are defined hereinbefore, and each may be cyclic, or may together be cyclizable. To generate the alkoxide ion during the overall reaction of this process, it is critical that the trihalomethyl group and the hydroxyl group be on the same carbon atom. It is preferred that Q be selected from the group consisting of chlorine and bromine, and chlorine is most preferred. A preferred α-trihalomethyl alcohol is selected from the group consisting of α-trihalomethylhydroxycycloalkanes, and α-trihalmethylhydroxyalkanes. Most preferred are lower α-trihalomethylhydroxyalkanes having from about 2 to about 6 carbon atoms. No other alkoxide ion generating agent, and no chloroform is necessary in this embodiment of the process. The overall reaction which occurs with different secondary amines may be represented as follows:

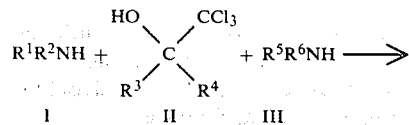

Then, with amine III the epoxide ring is opened to yield the product VII.

Typically the reactants are mixed into the organic phase, the order being unimportant. The aqueous alkali is then added to the system, with stirring, and heat is removed by cooling since the reaction is generally exothermic. The reaction proceeds at atmospheric pressure, and pressure considerations are not critical to the practice of the invention except as the requirements of a particular system may dictate.

Preferred organic solvents are essentially inert under the conditions of the reaction, and are immiscible in water. Most preferred are common aromatic and paraffinic solvents such as benzene, p-xylene, toluene, dichloromethane, chlorobenzene, cyclohexane and the like.

The invention is illustrated with the following examples:

EXAMPLE 1

α-phenyl, α-diethylaminodiethylacetamide, a compound of Groups A, E and K identified hereinbefore, and having the structure

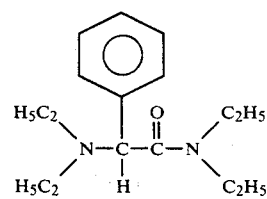

is prepared as follows: into a 500 ml three-necked flask fitted with a reflux condenser is placed 14.6 diethylamine and 100 ml dichloromethane, followed by 8.49 g benzaldehyde and 5.97 g chloroform. Then 0.57 g benzyltriethylammonium chloride (hereafter "BTEA" for brevity) is added, followed by the dropwise addition of 40 ml 50% NaOH. The addition took 2 min. The reaction was initiated at room temperature 22° C., but being exothermic, the temperature of the reaction mixture increased to about 42° C. and began refluxing. The reaction mixture cooled to room temperature in about 1 hr, and was allowed to continue to react for about 3.5 hr, after which it was worked up. Typically, a reaction mixture is worked up by extracting with dichloromethane, washing several times with water, drying and concentrating. Distillation yielded about 10.9 g of a light yellow oil at 160° C. at 0.3 mm Hg. The structure of the compound was confirmed by gas chromatographic (GC), infrared (IR), and nuclear magnetic resonance (NMR) analsis.

EXAMPLE 2

In a manner analogous to that described in Example 1 hereinabove, α-tolyl-α-propylamino-propylacetamide, a compound of Groups A,G and M identified hereinabove, and having the structure

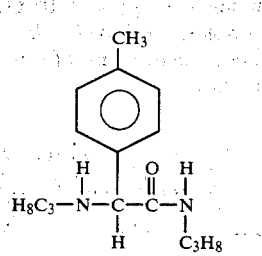

is prepared by reacting propylamine with p-methyl-benzaldehyde and chloroform.

EXAMPLE 3

In a manner analogous to that described in Example 1 hereinabove, α-phenyl-N-methylanilino-N-methylacetanilide, a compound of Groups A, I and O identified hereabove, and having the structure

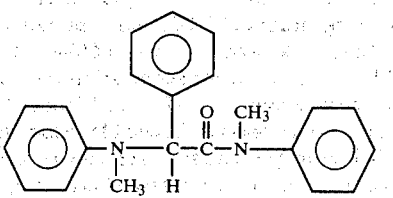

is prepared by reacting N-methylaniline, benzaldehyde and chloroform.

EXAMPLE 4

A. α-dimethyl, α-o-toluidinyl, diethylacetamide, a compound of Groups B, F and K identified hereinbefore, and having the structure

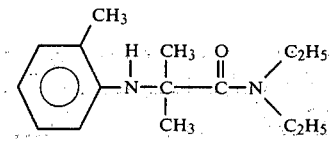

is prepared as follows: Into a 500 ml three-necked flask fitted with a reflux condenser is placed 10.72 g o-toluidine and 100 ml dichloromethane, followed by 14.6 g diethylamine, 8.7 g acetone and 11.94 g chloroform. Then 1.14 g "BTEA" is added, followed by the dropwise addition of 40 ml 50% NaOH. The reaction was run in an ice-bath to keep the temperature below 10° C. The addition took 1 hr. The reaction was slightly exothermic and was run in the ice-bath until the ice melted. The reaction was run for 3 hr at a temperature below 10° C. The reaction mixture is worked up after 5 hrs. The oil obtained was triturated with pentane and chilled in a refrigerator to yield 7.7 g of white crystals. The filtrate was concentrated and cooled, and an additional 2.5 g of white crystals were obtained. Recrystallization of all the crystals from pentane gave 7.5 g of white crystals, melting point 77°-79° C.

B. In a manner analogous to that described in Example 4A hereinabove, α-dimethyl, α-p-toluidinyldiethylacetamide, another compound of Groups B, F and K, having the structure

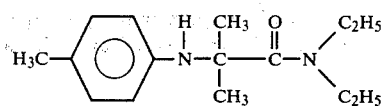

is prepared as follows: 10.72 g p-toluidine and 100 ml dichloromethane are mixed in a 500 ml three-necked flask followed by the addition of 8.7 g acetone, 11.94 g chloroform and 10.95 g diethylamine, and 1.14 g BTEA added dropwise. Then 40 ml 50% NaOH is added dropwise while stirring. The reaction was run in an ice-bath to keep the temperature below 10° C. The reaction was slightly exothermic and the temperature remained around 8° during addition. The addition took 1 hr 35 min. Upon working up after about 3 hr, 20 g of solid reaction product is obtained which is washed thoroughly with hexane. Recrystallization from a mixture of benzene and hexane yields 10.2 g light yellow crystals having a melting point of 123.5°-126.5°. Additional crystals are collected from the mother liquor, and all the crystals are recrystallized to yield white needles m.pt. 126°-127° C. The above structure is confirmed by GC, IR, and NMR analysis.

C. In a manner analogous to that described in the foregoing examples, α-dimethyl, α-p-phenetidinodiethylacetamide, another compound of Groups B, F and K, having the structure

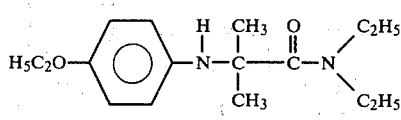

is prepared as follows: The following reactants are mixed in amounts set forth hereinafter, in a three-necked flask containing 100 ml dichloromethane: 13.72 g p-phenetedine, 11.6 g acetone, and 22.5 g dimethylamine. 60 ml 50% NaOH and 12.54 g chloroform are added dropwise, then 1.14 g BTEA is added. The reaction is again run in an ice-bath and the reaction further worked up as before. Recrystallization from benzene-pentane yields about 4 g of yellow crystalline needles. The above-identified structure is confirmed by GC, IR, and NMR analysis.

D. In a manner analogous to that described in Example 4 hereinabove, a compound of Groups B, F and K, identified as α-dimethyl, α-anilinodiethyl-acetamide, having the structure

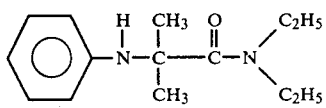

is prepared as follows: The following reactants are mixed in amounts set forth hereafter in an ice-bath cooled three-necked flask containing 100 ml dichloromethane: 7.31 g diethylamine, 11.6 g acetone, 11.9 g chloroform. While stirring, add 9.77 g aniline followed by 1.14 g TBEA, then 40 ml 50% NaOH dropwise. Upon workup 15.5 g off-white crystalline solid is obtained which is recrystallized from benzene-hexane.

EXAMPLE 5

In a manner analogous to that described in the foregoing examples, α-dimethyl,α-anilinopropylacetamide, another compound of Groups B, F and M, having the structure:

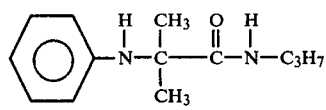

is prepared as follows: The following reactants are mixed in amounts set forth hereinafter in a three-necked flask containing 100 ml dichloromethane: 9.3 g aniline, 11.6 g acetone, 11.9 chloroform. 8.87 g isopropylamine and 2.24 BTEA are added dropwise while stirring. The reaction is commenced upon addition of 40 ml 50%NaOH dropwise at ice-bath temperature which keeps the reaction temperature below 10° C. Upon work-up, 11.4 g of a light yellow oil distills over at 110°–120° C. at a pressure of 0.4 mm.

EXAMPLE 6

In a manner analogous to that described in Example 5 hereinabove, a compound of Groups B, F and N, identified as α-dimethyl-α-anilino-dicyclohexylacetamide having the structure

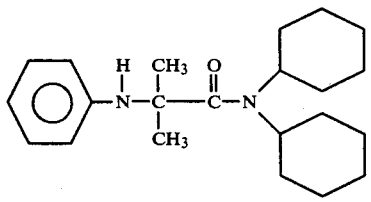

is prepared by reacting aniline, with dicyclohexylamine, acetone and chloroform utilizing a slight excess of chloroform and substantially stoichiometric quantities of the other reactants. The example is repeated keeping essentially the same reaction conditions and quantities of reactants, except that Aliquat TM 336, a tetra-alkyl ammonium salt, more precisely N-methyl-N,N,N-tri(-mixed $C_8$–$C_{10}$ alkyl)ammonium chloride, is used. The same substituted acetamide reaction product obtained with BTEA catalyst is again produced and recovered after working up.

EXAMPLE 7

In a manner analogous to that described in Example 6 hereinabove, a compound of Groups D, F and L, identified as α-pentamethylene, α-toluidinotolylacetamide, having the structure

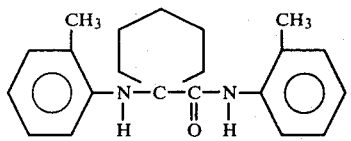

is prepared by the reaction of aniline with chloroformand cyclohexanone in the presence of an onium salt catalyst. A solid reaction product is obtained which is recrystallized from hexane. The crystals obtained have a melting point of 176°–179° C.

EXAMPLE 8

A. In a manner analogous to that described in the foregoing examples, α-dimethyl,α-4-chloroanilino-4-chloroacetanilide, a compound of Groups B, F and L, having the structure

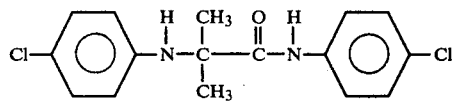

is prepared as follows: In a 500 ml three-necked flask equipped with an air stirrer, thermometer and dropping funnel, is placed 25.54 g 4-chloroaniline and 100 ml dichloromethane, followed by 8.7 g acetone and 13.13 g chloroform. In this, as in other reactions hereinabove in which $CHCl_3$ is used, only a slight excess of $CHCl_3$ is used, because a greater excess produces undesirable side reactions. 0.68 g BTEA is added and 40 ml 50% NaOH is dropped into the flask, slowly, to keep the temperature of the exothermic reaction, which commences at ice-bath temperature of 0° C., from rising above 10° C. The reaction is allowed to run until the ice is melted (about 2 hr). The flask is removed from the water bath, stirred at room temperature (22° C.) for about 3 hr, and worked up. A dark oil was distilled to remove all impurities at below 60° C. under vacuum. Upon triturating with hot hexane a solid is obtained which upon recrystallization from benzene-hexane yields 13.5 g of a greyish solid.

The structure hereinabove is confirmed by GC, IR, mass spectrometer data and NMR analysis.

B. In a manner analogous to that described in the foregoing examples, another compound of Groups B, F and L identified as phenylaminoisobutyric acid anilide, also referred to as α-dimethyl, α-anilino-acetanilide, having the structure

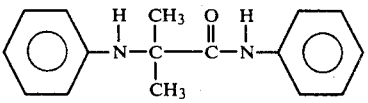

is prepared as follows: The following reactants are mixed in amounts set forth hereinafter in an ice-bath cooled three-necked flask containing 100 ml dichloromethane: 18.6 g aniline, 14.5 g acetone, 12.04 g chloroform. While stirring, add 1.14 g BTEA, then 40 ml 50% NaOH dropwise. Upon workup 16.0 g of a white solid is obtained free of isonitrile, after drying overnight.

C. In a manner analogous to that described in the foregoing examples, another compound of Groups B, F and L identified as α-dimethyl,α-toluidino-o-methylacetanilide, having the structure

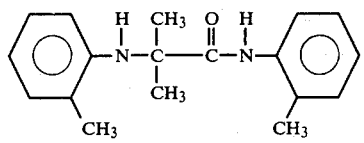

is prepared as follows: The following reactants are mixed in amounts set forth hereafter in an ice-bath cooled three-necked flask containing 100 ml dichloromethane: 21.43 g o-toluidine, 11.6 g acetone, 11.94 g chloroform. While stirring, add 1.14 g BTEA, then 40 ml 50% NaOH dropwise. Upon workup 10.5 g of colorless crystals are obtained.

D. In a manner analogous to that described in the foregoing examples, another compound of Groups B,F and L identified as α-dimethyl-α-p-toluidino-p-methylacetanilide, having the structure

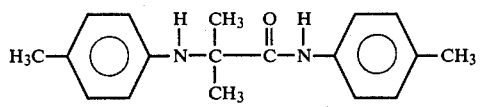

is prepared as follows: The following reactants are mixed in amounts set forth hereafter in an ice-bath cooled three-necked flask containing 100 ml dichloromethane: 21.56 g p-toluidine, 29.0 g acetone, 11.94 g chloroform. While stirring, add 1.14 g BTEA, then 40 ml 50% NaOH dropwise. Upon workup including washing with pentane, 23.4 g of a white solid is obtained after drying overnight.

E. In a manner analogous to that described in the foregoing examples, another compound of Groups B, G and L identified as α-dimethyl,α-p-phenetidino-p-ethoxyacetanilide, having the structure

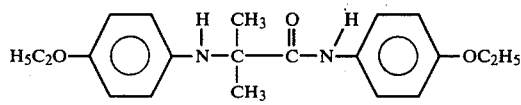

is prepared as follows: The following reactants are mixed in amounts set forth hereafter in an ice-bath cooled three-necked flask containing 100 ml dichloromethane: 12.5 p-phenetidine, 3.0 g acetone, 5.6 g chloroform, and 0.34 BTEA. While stirring, add 24 ml 50% NaOH dropwise. Upon workup including washing with hexane, 15.3 g of a yellow solid is obtained after drying overnight.

EXAMPLE 9

In a manner analogous to that described in the foregoing example 4A, a compound α-methylα-phenyl-α-anilino-acetanilide of Groups C, F, and L identified hereinabove, having the structure

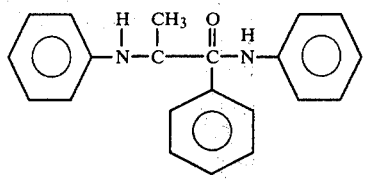

is prepared by reacting aniline with acetophenone and chloroform using Aliquat*336 as the onium salt catalyst.

EXAMPLE 10

The substituted acetamide reaction products obtained using acetone as a reactant in the examples hereinabove are also obtained by substituting acetone cyanohydrin for acetone, and using a slight excess over two equivalents of chloroform. The reaction may be carried out in the absence of solvent. Repetition of this example with bromoform instead of chloroform also gives the same substituted acetamide product. Good yields are obtained irrespective of the onium salt used, provided it has adequate solubility.

EXAMPLE 11

Phenylaminoisobutyric acid anilide prepared in Example 8B hereinabove is also prepared by reacting aniline with α-trichloromethyl-2-propanol in an amount about 25% in excess over stoichiometric, in the presence of BTEA in toluene solvent. No chloroform or acetone is necessary. The reaction proceeds at ice-bath temperature and is slightly exothermic.

This example is repeated using Aliquat*336 instead of BTEA; and, again using tributyl hexadecyl phosphonium bromide or tetrabutyl ammonium hydrosulfate as the onium salt catalysts.

EXAMPLE 12

In a manner analogous to that described in Example 8A hereinabove, α-dimethyl, α-dimethyl α-morpholino-acetamorpholinide, a compound of Groups B, J and P identified hereinabove, having the structure

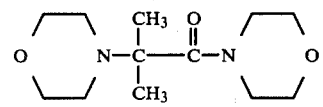

is prepared by the reaction of morpholine, acetone and chloroform catalyzed by a phosphonium salt, specifically by $(C_4H_9)_3P^+C_{16}H_{33}Cl^-$ in aqueous NaOH. A solid reaction product is formed which is recrystallized from heptane to yield crystals having a melting point of 56°–59° C.

The efficacy of substituted acetamides as antioxidants to retard oxidative degradation of synthetic natural rubber (SNR) is measured by ASTM-D-1646–72 testing procedure. The SNR used was obtained by solution polymerization of isoprene which yielded about 99% 1-4 cis addition product and 0.8% trans 1-4 addition product. The level of antioxidant used is 1 part per 100 parts SNR in all tests, using a large rotor and 1 min warm-up time. Mooney buttons were aged at 70° C. for 10 days in an oven in accordance with testing procedure ASTM-D-573-67.

The control was Stalite*S p,p'-dioctyl-diphenylamine, an antioxidant commercially available from The B. F. Goodrich Company, Akron, Ohio. The percent change in Mooney viscosity recorded in Table I hereinbelow, is the measure of antioxidant effectiveness; the lower the percent change, the more effctive is the antioxidant.

TABLE I

| Compound identification | % change in Mooney viscosity |
|---|---|
| 1. Stallite*S(control) | 14.3 |
| 2. α-dimethyl,α-p-phenetidino-p-ethoxyacetanilide | 10.4 |
| 3. α-dimethyl,α-p-toluidino-methylacetanilide | 11.2 |
| 4. α-dimethyl,α-p-phenetidino-diethylacetanilide | 15.2 |
| 5. NONE | infinite** |

**cannot be measured

The efficacy of substituted acetamides as antioxidants and stabilizers against heat degradation of a functional fluid such as a synthetic ester lubricant is evaluated according to a modified Federal Test Method Standard Number 791a, Method 5308.5 (July 27, 1964). This is an oxidation test at 215.5° C. (420° F.) of a functional fluid containing a stabilizer which is simply blended into the fluid. The test is performed in the presence of air and 5 different metals such as copper, silver, magnesium, aluminum and steel. The test fluid chosen is di(2-ethylhexyl)sebacate (available from Hercules Chemical Company, Wilmington, Del. under the trade mark Herculube A). The fluid is poured into a large test tube equipped with an air bubbler, a holder for the metals and a condenser. The test tube is placed in a heated block and the temperature raised to 215.5° C. Air is then bubbled through the fluid at a rate of about 5 liters per hour over a 72 hour interval. At the end of each test, the sample is evaluated by:

(a) visual examination of the fluid for the amount of sludge formed, if any;

(b) measuring the percent change in viscosity from the preoxidation level;

(c) measuring the change in the acid number of the oxidized fluid;

(d) measuring the change in weight of the metals after oxidation; and, (e) measuring the percent loss, if any, in the weight of the oxidized fluid.

The measure of stability of the stabilized fluid is determined by comparison with a control sample of the fluid which is stabilized with 0.75 parts (phr) of p,p'-dioctyl-diphenylamine (commercially available under the trademark Stalite S from the B. F. Goodrich Company, Akron, Ohio), per 100 parts of synthetic ester functional fluid. Some of the test data obtained are set forth in Table II hereinbelow.

TABLE II

| | Compound | conc. of stabilizer (phr) | sludge formation | Viscosity change (%) |
|---|---|---|---|---|
| 1. | p,p'-dioctyl diphenylamine (Stalite*S) Cintrol | 1.5 | none | 21 |
| 2. | α-dimethyl,α-anilinodiethylacetamide | 1.5 | slight | 9.4 |
| 3. | α-dimethyl,α-p-phenetidinodibutylacetamide | 1.5 | none | 6.8 |
| 4. | α-dimethyl,α-p-toluidinodiethylacetamide | 1.5 | slight | 6.7 |
| 5. | α-dimethyl,α-p-toluidino-p-methylacetanilide | 1.5 | slight | 8.6 |
| 6. | None | 0.0. | heavy | 127.6 |
| 7. | α-dimethyl,α-anilinoacetanilide and Stalite*S | 0.75 0.75 | none | 10.5 |
| 8. | α-dimethyl,α-anilinodiethylacetamide and Stalite*S | 0.75 0.75 | none | 11.2 |
| 9. | α-pentamethylene,α-anilino-acetanilide and Stalite*S | 0.75 0.75 | none | 12.8 |
| 10. | α-dimethyl-α-morpholino-acetamorpholinide and Stalite*S | 0.75 0.75 | none | 9.7 |

I claim:

1. A stabilized composition of matter which comprises a synthetic lubricant subject to the deleterious effects of oxygen and heat and from about 0.001 percent to about 10 percent by weight of a substitued α-aminoacetamide of the formula

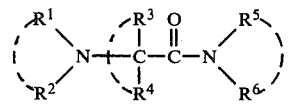

wherein $R^1$, $R^2$, $R^3$, $R^4$, $R^5$ and $R^6$ independently represent the following substituents: hydrogen; aryl, alkyl having from 1 to about 24 carbon atoms wherein functional groups may be substituted with alkyl groups; hydroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; alkenyl and aralkyl having from 7 to about 14 carbon atoms; alkylene having from 1 to about 7 carbon atoms; alkenylene having from 2 to about 10 carbon atoms; each substituent optionally containing a phosphite, ester or hindered phenol group, except that each amine and amide N atom has at least one substituent, and said each substituent in combination, $R^1$ with $R^2$, $R^3$ with $R^4$, and $R^5$ with $R^6$, optionally (i) forms a ring containing from about 5 to about 9 ring atoms, which ring optionally (ii) contains a hetero atom selected from the group consisting of N, S and O, and a moiety selected from the group consisting of keto, ester, amide, thio and ether.

2. The stabilized composition of matter of claim 1 wherein one of $R^3$ and $R^4$ is H.

3. The stabilized composition of matter of claim 1 wherein $R^3$ and $R^4$ are each acyclic.

4. The stabilized composition of matter of claim 1 wherein one of $R^3$ and $R^4$ is acyclic and the other is cyclic.

5. The stabilized composition of matter of claim 1 wherein $R^3$ and $R^4$ are cyclized.

6. The stabilized composition of matter of claim 1 wherein $R^1$ and $R^2$ are acyclic.

7. The stabilized composition of matter of claim 1 wherein one of $R^1$ and $R^2$ is cyclic the ring having from about 5 to about 9 ring members.

8. The stabilized composition of matter of claim 1 wherein one of $R^1$ and $R^2$ is acyclic.

9. The stabilized composition of matter of claim 1 wherein $R^1$ and $R^2$ is each cyclic the ring having from about 5 to about 9 ring members.

10. The stabilized composition of matter of claim 1 wherein one of $R^1$ and $R^2$ is acyclic, and the other cyclic, the ring having from about 5 to about 9 ring members.

11. The stabilized composition of matter of claim 1 wherein $R^1$ and $R^2$ are cyclized, the ring having from about 5 to about 9 ring members.

12. The stabilized composition of matter of claim 1 wherein $R^5$ and $R^6$ are each acyclic.

13. The stabilized composition of matter of claim 1 wherein one of $R^5$ and $R^6$ is cyclic, the ring having from about 5 to about 9 ring members.

14. The stabilized composition of matter of claim 1 wherein one of $R^5$ and $R^6$ is acyclic.

15. The stabilized composition of matter of claim 1 wherein $R^5$ and $R^6$ are each cyclic, each ring having from about 5 to about 9 ring members.

16. The stabilized composition of matter of claim 1 wherein one of $R^5$ and $R^6$ is acyclic, and the other cyclic, the ring having from about 5 to about 9 ring members.

17. The stabilized composition of matter of claim 1 wherein $R^5$ and $R^6$ are cyclized, the ring having from about 5 to about 9 ring members.

18. The stabilized composition of matter of claim 1 wherein the organic material is lubricant comprising a synthetic polycarboxylate type ester functional fluid.

19. A catalytic method for directly preparing a substituted α-aminoacetamide having the formula

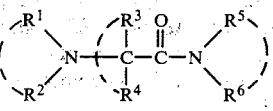

wherein $R^1$, $R^2$, $R^3$, $R^4$, $R^5$ and $R^6$ independently represent the following substituents: hydrogen; aryl, alkyl having from 1 to about 24 carbon atoms wherein functional groups may be substituted with alkyl groups; hydroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; alkenyl and aralkyl having from 7 to about 14 carbon atoms; alkylene having from 1 to about 7 carbon atoms; alkenylene having from 2 to about 10 carbon atoms; each substituent optionally containing a phosphite, ester or hindered phenol group, except that each amine and amide N atom has at least one substituent, and said each substituent in combination, $R^1$ with $R^2$, $R^3$ with $R^4$, and $R^5$ and $R^6$, optionally (i) forms a ring containing from about 5 to about 9 ring atoms, which ring optionally (ii) contains a hetero atom selected from the group consisting of N, S and O, and a moiety selected from the group consisting of keto, ester, amide, thio and ether, comprising reacting (a) an amine nucleophilic agent with (b) an alkoxide ion generating agent and (c) a dichlorocarbene generating agent, in an aqueous alkaline medium, at a relatively low temperature in the range from about −20° C. to about 50° C., in the presence of a catalytic amount of an onium salt sufficient to yield said substituted α-aminoacetamide.

20. The catalytic method of claim 19 wherein said amine nucleophilic agent is selected from the group consisting of primary and secondary amines, said alkoxide ion generating agent is selected from the group consisting of ketones, aldehydes and cyanohydrins, and said dichlorocarbene generating agent is chloroform.

21. The catalytic method of claim 20 wherein said onium salt has the formula $$R_nY^+X^-$$

wherein

Y is selected from the group consisting of N, P and S;

R represents either different of identical monovalent organic radicals bonded to Y;

$X^-$ is a counterion selected from the group consisting of Cl, Br, I, F, $SO^=_4$ and $HSO_4^=$; and, n is an integer which is 3 when Y is S, and which is 4 when Y is N or p.

22. The catalytic method of claim 21 wherein said onium salt has the formula $$(R_aR_bR_cR_dY^+)X^-$$

wherein:

Y is N or P, and $R_a$–$R_d$ are monovalent hydrocarbon radicals selected from the group consisting of alkyl, alkenyl, aryl, alkaryl, aralkyl, and cycloalkyl radicals, optionally substituted with suitable heteroatom-containing functional groups.

23. The catalytic method of claim 22 wherein said onium salt is a quaternary onium salt of N or P and the total number of carbon atoms is in the range from about 15 to about 40.

24. A catalytic method for directly preparing a substituted α-aminoacetamide having the formula

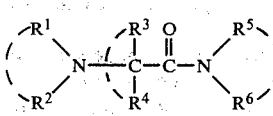

wherein $R^1$, $R^2$, $R^3$, $R^4$, $R^5$ and $R^6$ independently represent the following substituents: hydrogen; aryl, alkyl having from 1 to about 24 carbon atoms wherein functional groups may be substituted with alkyl groups; hyroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; hydroxyalkyl ether or cyanoalkyl ether groups having from 4 to about 18 carbon atoms; alkenyl and aralkyl having from 7 to about 14 carbon atoms; alkylene having from 1 to about 7 carbon atoms; alkenylene having from 2 to about 10 carbon atoms; each substituent optionally containing a phosphite, ester or hindered phenol group, except that each amine and amide N atom has at least one substituent, and said each substituent in combination, $R^1$ with $R^2$, $R^3$ with $R^4$, and $R^5$ with $R^6$, optionally (i) forms a ring containing from about 5 to about 9 ring atoms, which ring (ii) contains a hetero atom selected from the group consisting of N, S and O, and a moiety selected from the group consisting of keto, ester, amide, thio and ether, comprising reacting (i) an amine nucleophilic agent with (ii) an α-trihalmethylhydroxy alcohol, in an aqueous alkaline medium, at a relatively low temperature in the range from about −20° C. to about 50° C., in the presence of a catalytic amount of an onium salt sufficient to yield said substituted aminoacetamide.

25. The cataytic method of claim 24 wherein said amine nucleophilic agent is selected from the group consisting of primary and secondary amines, and said α-trihalomethyl alcohol is selected from the group consisting of α-trihalomethylhydroxyalkanes and α-trihalomethylhydroxycycloalkanes.

26. A substituted α-aminoacetamide compound of the formula

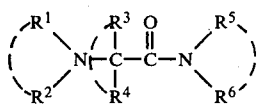

wherein $R^1$, $R^2$, $R^3$, $R^4$, $R^5$ and $R^6$ independently represent the following substituents: aryl, alkyl having from 1 to about 24 carbon atoms wherein functional groups may be substituted with alkyl groups; hyroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; aralkyl having from 7 to about 14 carbon atoms; alkylene having from 1 to about 7 carbon atoms; alkenylene having from 2 to about 10 carbon atoms; and $R^1$, $R^2$, may in addition independently represent hydrogen; each substituent optionally containing a phosphite, ester or hindered phenol group, except that substituents on the amine N atom are different from substituents on the amide N atom, and said substituents in combination, $R^1$ with $R^2$, $R^3$ with $R^4$, and $R^5$ with $R^6$, optionally (i) forms a ring containing from about 5 to about 9 ring atoms, which ring optionally (ii) contains an O hetero atom.

27. The compound of claim 26 wherein one of $R^1$ and $R^2$ is H and the other selected from the group consisting of aryl, aralkyl and alkaryl; and, $R^5$ and $R^6$ are each alkyl.

28. The compound of claim 26 wherein $R^1$ and $R^2$ are cyclized forming a ring, said heteroatom therein is O, and $R^5$ and $R^6$ are similarly cyclized.

29. A substituted α-aminoacetamide compound of the formula

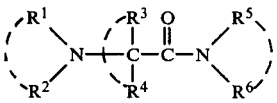

wherein $R^1$, $R^2$, $R^3$, $R^4$, $R^5$ and $R^6$ independently represent the following substituents: aryl, alkyl having from 1 to about 24 carbon atoms wherein functional groups may be substituted with alkyl groups; hydroxyalkyl having from 1 to about 12 carbon atoms; haloalkyl having from 1 to about 12 carbon atoms; cyanoalkyl having from 2 to about 12 carbon atoms; aminoalkyl or iminoalkyl having from 1 to about 12 carbon atoms; ether groups having from 3 to about 18 carbon atoms; aralkyl having from 7 to about 14 carbon atoms; alkylene having from 1 to about 7 carbon atoms; alkenylene having from 2 to about 10 carbon atoms; and $R^1$, $R^2$, may in addition independently represent hydrogen; each substituent optionally containing a phosphite, ester or hindered phenol group, except that substituents on the amine N atom are different from substituents on the amide N atom, and said substituents in combination, $R^1$ with $R^2$, $R^3$ with $R^4$, and $R^5$ with $R^6$, optionally (i) forms a ring containing from about 5 to about 9 ring atoms, which ring optionally (ii) contains hetero atoms selected from the group consisting of N, S and O, and a moiety selected from the group consisting of keto, ester, amide, thio and ether.

30. The compound α-dimethyl-α-p-toluidino-p-methylacetanilide.

31. A catalytic method for directly preparing α-dimethyl-α-p-toluidino-p-methylacetanilide having the formula

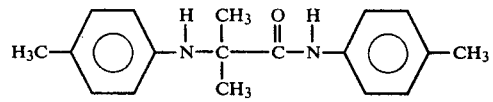

comprising reacting (a) p-toluidine, (b) an alkoxide ion generating agent selected from the group consisting of ketone, aldehyde and cyanohydrin, and (c) a dichlorocarbene generating agent selected from the group consisting of bromoform, chloroform and iodoform, in an aqueous alkaline medium, at a relatively low temperature in the range from about −20° C. to about 50° C., in the presence of a catalytic amount of an onium salt sufficient to yield said α-dimethyl-α-p-toluidino-p-methylacetanilide.

32. A stabilized composition of matter which comprises a synthetic polycarboxylate type ester functional fluid subject to the deleterious effects of oxygen and heat and from about 0.001 percent to about 10 percent by weight of α-dimethyl-α-p-toluidino-p-methylacetanilide.

33. The compound of claim 26 wherein $R^1$, $R^2$, $R^5$, and $R^6$ independently represent hydrogen, said aryl and said alkyl; and, $R^3$ and $R^4$ represent said aryl and alkyl, optionally forming an alkylene ring containing from 5 to about 9 carbon atoms.

34. The compound of claim 33 wherein when one of $R^3$ and $R^4$ is said alkyl, the other is selected from said alkyl and said aryl.

35. The compound of claim 33 wherein one of $R^1$ and $R^2$ is said aryl, one of $R^5$ and $R^6$ is said aryl, and $R^4$ is said aryl.

* * * * *